United States Patent
Tiernan et al.

(10) Patent No.: US 11,898,170 B2
(45) Date of Patent: Feb. 13, 2024

(54) CELL CULTURE METHODS INVOLVING HDAC INHIBITORS OR REP PROTEINS

(71) Applicant: Ultragenyx Pharmaceutical Inc., Novato, CA (US)

(72) Inventors: Aubrey R. Tiernan, Somerville, MA (US); Christopher Tipper, Cambridge, MA (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 784 days.

(21) Appl. No.: 16/496,110

(22) PCT Filed: Mar. 22, 2018

(86) PCT No.: PCT/US2018/023841
§ 371 (c)(1),
(2) Date: Sep. 20, 2019

(87) PCT Pub. No.: WO2018/175775
PCT Pub. Date: Sep. 27, 2018

(65) Prior Publication Data
US 2020/0032221 A1 Jan. 30, 2020

Related U.S. Application Data

(60) Provisional application No. 62/475,112, filed on Mar. 22, 2017.

(51) Int. Cl.
| | | |
|---|---|---|
| *C12N 7/02* | (2006.01) | |
| *C12N 15/864* | (2006.01) | |
| *C12N 15/63* | (2006.01) | |
| *C12N 15/34* | (2006.01) | |
| *C12N 7/00* | (2006.01) | |
| *C12N 15/86* | (2006.01) | |

(52) U.S. Cl.
CPC .............. *C12N 7/00* (2013.01); *C12N 15/86* (2013.01); *C12N 2330/51* (2013.01); *C12N 2510/02* (2013.01); *C12N 2511/00* (2013.01); *C12N 2750/14122* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | |
|---|---|---|
| 5,387,484 A | 2/1995 | Doany et al. |
| 5,658,785 A | 8/1997 | Johnson |
| 5,688,676 A | 11/1997 | Zhou et al. |
| 5,691,176 A | 11/1997 | Lebkowski et al. |
| 5,741,683 A | 4/1998 | Zhou et al. |
| 5,872,005 A | 2/1999 | Wang et al. |
| 6,004,797 A | 12/1999 | Colosi |
| 6,127,175 A | 10/2000 | Vigne et al. |
| 6,156,303 A | 12/2000 | Russell et al. |
| 6,489,162 B1 | 12/2002 | Shenk et al. |
| 6,566,118 B1 | 5/2003 | Atkinson et al. |
| 6,723,551 B2 | 4/2004 | Kotin et al. |
| 6,753,419 B1 | 6/2004 | Toniatti et al. |
| 6,846,665 B1 | 1/2005 | Horer et al. |
| 6,943,019 B2 | 9/2005 | Wilson et al. |
| 7,271,002 B2 | 9/2007 | Kotin et al. |
| 7,510,872 B2 | 3/2009 | Clark et al. |
| 8,163,543 B2 | 4/2012 | Urabe et al. |
| 8,409,842 B2 | 4/2013 | Clark et al. |
| 8,512,981 B2 | 8/2013 | Hermens et al. |
| 8,980,247 B2 | 3/2015 | Meyers et al. |
| 2002/0081721 A1 | 6/2002 | Allen et al. |
| 2002/0115189 A1 | 8/2002 | Natsoulis et al. |
| 2002/0127582 A1 | 9/2002 | Atkinson et al. |
| 2004/0235173 A1 | 11/2004 | Bleck et al. |
| 2005/0112765 A1 | 5/2005 | LI et al. |
| 2005/0148076 A1 | 7/2005 | Allen |
| 2006/0013063 A1 | 1/2006 | Singh |
| 2008/0166758 A1* | 7/2008 | Engelhardt ............. A61P 43/00 435/235.1 |
| 2010/0248355 A1 | 9/2010 | Atkinson et al. |
| 2011/0251547 A1 | 10/2011 | Xing et al. |
| 2012/0058917 A1 | 3/2012 | Gaken et al. |
| 2012/0122718 A1* | 5/2012 | Reisman ............ G01N 33/5011 435/320.1 |
| 2014/0056919 A1 | 2/2014 | Xing et al. |
| 2014/0359799 A1 | 12/2014 | Wang et al. |
| 2015/0024467 A1 | 1/2015 | Sheldon et al. |

(Continued)

FOREIGN PATENT DOCUMENTS

| | | |
|---|---|---|
| WO | WO-9617947 A1 | 6/1996 |
| WO | WO-0024916 A1 | 5/2000 |
| WO | WO-0047757 A1 | 8/2000 |

(Continued)

OTHER PUBLICATIONS

Kim et al., Enhancement of Transgene Expression by HDAC Inhibitors in Mouse Embryonic Stem Cells, Dev. Reprod. vol. 17, No. 4 , 379-387, Dec. 2013.*

Nakowitsch et al., Optimization of Baculovirus Transduction on FreeStyleTM293 Cells for the Generation of Influenza B/Lee/40, Molecular Biotechnology, 2006, pp. 157-164.*

Clement and Greiger, Manufacturing of recombinant adeno-associated viral vectors for clinical trials, Methods & Clinical Development (2016) pp. 1-7.*

(Continued)

*Primary Examiner* — Maria Marvich
(74) *Attorney, Agent, or Firm* — Goodwin Procter LLP

(57) ABSTRACT

The invention relates to methods of culturing cells, generating cell lines, and delivering polynucleotides to cells involving the use of HDAC inhibitors and/or adeno-associated virus (AAV) rep proteins.

10 Claims, 3 Drawing Sheets

(56) References Cited

U.S. PATENT DOCUMENTS

2015/0353899 A1   12/2015   Pechan et al.
2018/0044698 A1*   2/2018   Srivastava ............. C12N 15/86

FOREIGN PATENT DOCUMENTS

WO   WO2014/201252 A2   12/2014
WO   WO-2016/134337 A1   8/2016

OTHER PUBLICATIONS

Van Tendeloo et al., Highly efficient gene delivery by mRNA electroporation in human hematopoietic cells: superiority to lipofection and passive pulsing of mRNA and to electroporation of plasmid cDNA for tumor antigen loading of dendritic cells, Blood, 2001, 49-56.*

Escandell et al., Towards a scalable bioprocess for rAAV production using a HeLa stable cell line, Biotechnol Bioeng. 2023;1-10.*

Liu et al., Selective Rep-Cap Gene Amplification as a Mechanism for High-Titer Recombinant AAV Production from Stable Cell Lines, Molecular Therapy, 2000, pp. 394-403.*

Clark et al., Cell lines for the Production of Recombinatn Adeno-Associated Virus, Human Gene Therapy 6:1329-1341 (Oct. 1995).*

Xiang et al., A method mediated AAVS1 recombination with Rep mRNA and homologous arms, Acta Biochim Biophys Sin 2012, 44: 1015-1022.*

Clement and Grieger, Manufacturing of recombinant adeno-associated viral vectors for clinical trials, Molecular Therapy Methods & Clinical Development (2016) pp. 1-7.*

Clark et al., "Cell lines for the production of recombinant adeno-associated virus", Human Gene Therapy. vol. 6, (1995), pp. 1329-1341.

Conway et al., "High-titer recombinant adeno-associated virus production utilizing a recombinant herpes simplex virus type I vector expressing AAV-2 rep and cap", Gene Therapy. vol. 6, No. 6, (1999), pp. 986-993.

Ding et al., "High-throughput nuclear delivery and rapid expression of DNA via mechanical and electrical cell-membrane disruption", Nat. Biomed. Eng. vol. 1, (2017), pp. 1-15.

Howden et al., "The transient expression of mRNA coding for rep protein from AAV facilitates targeted plasmid integration", The Journal of Gene Medicine. vol. 10, (2008), pp. 42-50.

Martin et al., "Generation and Characterization of Adeno-Associated Virus Producer Cell Lines for Research and Preclinical Vector Production", Human Gene Therapy Methods. vol. 24, (2013), pp. 253-269.

Sharei et al., "Cell squeezing as a robust, microfluidic intracellular delivery platform", Journal of Visualized Experiments (81), (2013) pp. 1-7.

Strobel et al., "Comparative Analysis of Cesium Chloride- and Iodixanol-Based Purification of Recombinant Adeno-Associated Viral Vectors for Preclinical Applications", Human Gene Therapy Methods. vol. 26, No. 4, (2015), pp. 147-157.

Thorne et al., "Manufacturing recombinant adeno-associated viral vectors from producer cell clones", Human Gene Therapy. vol. 20, (2009), pp. 707-714.

Virag et al., "Producing Recombinant Adeno-Associated Virus in Foster Cells: Overcoming Production Limitations Using a Baculovirus-Insect Cell Expression Strategy", Human Gene Therapy. vol. 20, No. 8 (2009), pp. 807-817.

Wang et al., "Identification of an adeno-associated virus binding epitope for AVB sepharose affinity resin", Molecular Therapy—Methods and Clinical Development. vol. 2, (2015), pp. 1-6.

Wright, "Review: Transient Transfection Methods for Clinical Adeno-Associated Viral Vector Production", Human Gene Therapy. vol. 20, (2009), pp. 698-706.

Zhen et al., "Infectious titer assay for adeno-associated virus vectors with sensitivity sufficient to detect single infectious events", Human Gene Therapy. vol. 15, (2004), pp. 709-715.

Li et al. "Role for Highly Regulated rep Gene Expression in Adeno-Associated Virus Vector Production" vol. 71, No. 7, Journal of Virology, Jul. 1997, pp. 5236-5243.

Xiang et al. "A method mediated AAVS1 recombination with Rep mRNA and homologous arms", ACTA Biochim Biophys SIN, vol. 44, Oct. 3, 2012, pp. 1015-1022.

Howden et al. "The transient expression of mRNA coding for Rep protein from AAV facilitates targeted plasmid integration", The Journal of Gene Medicine, J Gene Med 2008, Jan. 1, 2007, pp. 42-50.

Howden et al. "Site-specific, Rep-mediated integration of the intact β-globin locus in the human erythroleukaemic cell line K562", Gene Therapy, May 22, 2008, pp. 1372-1383.

Youn et al. "Modified mRNA as an alternative to plasmid DNA (pDNA) for transcript replacement and vaccination therapy" Expert Opinion on Biological Therapy, Sep. 2, 2015, pp. 1337-1348.

Okada et al. "A Histone Deacetylase Inhibitor Enhances Recombinant Adeno-associated Virus-Mediated Gene Expression in Tumor Cells", Molecular Therapy, vol. 13, No. 4, Apr. 2006, pp. 738-746.

* cited by examiner

CELL CULTURE METHODS INVOLVING HDAC INHIBITORS OR REP PROTEINS

CROSS-REFERENCE TO RELATED APPLICATIONS

This application is a U.S. national stage application, filed under 35 U.S.C. § 371, of International Application No. PCT/US2018/023841 filed on Mar. 22, 2018, which claims the benefit of and priority to U.S. Provisional Patent Application No. 62/475,112, filed on Mar. 22, 2017, the entire contents of each of which are hereby incorporated by reference in their entirety for all purposes.

FIELD OF THE INVENTION

The invention relates to cell culture methods involving the use of HDAC inhibitors or adeno-associated virus (AAV) rep proteins.

BACKGROUND

Adeno-associated virus (AAV) is a non-pathogenic, replication-defective parvovirus. Recombinant AAV (rAAV) vectors have many unique features that make them attractive as vectors for gene therapy. In particular, rAAV vectors can deliver therapeutic genes to dividing and non-dividing cells, and these genes can persist for extended periods without integrating into the genome of the targeted cell. Given the widespread therapeutic applications of rAAV, it is useful to produce large quantities of the virus in a cost-effective manner. Stable eukaryotic cell lines can be generated by transfecting them with rAAV vectors, which preferentially integrate into the host genome on chromosome 19. However, typically, thousands of cell clones must be screened from multiple transfection runs to identify one producer cell line with a rAAV yield high enough for developing a cost-effective manufacturing process. Accordingly, there is a need for improved methods of generating stable cell lines that produce high yield of rAAV.

Wildtype AAV genomes encode four regulatory proteins called rep78, rep68, rep52, and rep40. These proteins cumulatively include site-specific DNA binding, ATP-dependent site-specific endonuclease, helicase, and ATPase activity, which orchestrate aspects of the viral life cycle. Typically, rAAV vectors are devoid of DNA sequences encoding rep proteins, and are composed of foreign DNA flanked by the 145 nucleotide-long AAV inverted terminal repeats (ITR). Often, rAAV are produced by means of a helper virus such as adenovirus.

SUMMARY OF THE INVENTION

It has now been discovered that delivery of an AAV rep mRNA can be used, for example, to enhance generation of rAAV stable cell lines and the titer of rAAV vectors harvested from these cells. Accordingly, one aspect of the invention provides a method of increasing rAAV vector titer or enhancing rAAV yield, e.g., from a eukaryotic or a host cell culture. The method includes co-delivering a rAAV vector with a rep mRNA (e.g., rep68 and/or rep78 mRNA) to a eukaryotic or host cell culture and harvesting rAAV from the cell culture.

In some embodiments, the co-delivery methods include liposome-based transfection. In some embodiments, the co-delivery methods include chemical-based transfection, such as methods using calcium phosphate, cationic polymers, DEAE-dextran, or activated dendrimers. In other embodiments, the co-delivery methods involve microinjection, electroporation, magnetic beads, nanoparticles, or cell squeezing.

Another aspect of the invention provides a method of generating or developing a cell line, e.g., a stable cell line for producing recombinant AAV (rAAV). The method includes co-delivering a rAAV vector with a rep mRNA (e.g., rep68 and/or rep78 mRNA) to a eukaryotic or host cell culture, followed by identifying a eukaryotic or host cell that contains the rAAV vector sequence integrated into the eukaryotic or host cell genome (e.g., by selecting cell colonies that have the rAAV vector integrated into the eukaryotic or host cell genome) and, optionally, harvesting the rAAV from the cell culture. In some embodiments, co-delivery of the rAAV with the rep mRNA enhances the titer of the harvested rAAV In some embodiments, the co-delivery methods include liposome-based transfection. In some embodiments, the co-delivery methods include chemical-based transfection, such as methods using calcium phosphate, cationic polymers, DEAE-dextran, or activated dendrimers. In other embodiments, the co-delivery methods involve microinjection, electroporation, magnetic beads or nanoparticles.

It has also been discovered that an HDAC inhibitor can be used, for example, to enhance integration of a recombinant polynucleotide into a eukaryotic or host cell genome, and/or increase yield of a gene product or viral vector from the eukaryotic or host cell. Accordingly, one aspect of the invention provides a method including co-delivering a recombinant polynucleotide with an HDAC inhibitor such as trichostatin A (TSA) to a eukaryotic or a host cell culture. In some embodiments, integration of the polynucleotide into a eukaryotic or host cell genome is detected and/or a stable eukaryotic or host cell line is generated. In some embodiments, one or more gene products are expressed in the eukaryotic or host cell culture. The gene products can be encoded by the recombinant polynucleotide or indirectly dependent on the presence of the recombinant polynucleotide. The gene products can be, for example, ribonucleic acids, peptides, or proteins. In some embodiments, the recombinant polynucleotide is a viral vector, including but not limited to a rAAV vector. Co-delivery of a recombinant viral vector with an HDAC inhibitor may enhance the integration of the viral vector into the host cell genome and increase the yield of viral vector harvested from the host cell.

In some embodiments, the co-delivery methods involve liposome-based transfection or chemical-based transfection, such as methods utilizing calcium phosphate, cationic polymers, DEAE-dextran, or activated dendrimers. In other embodiments, the co-delivery methods involve microinjection, electroporation, magnetic beads, nanoparticles, or cell squeezing.

These and other aspects and features of the invention are described in the following detailed description and claims.

DETAILED DESCRIPTION

Figure 1:
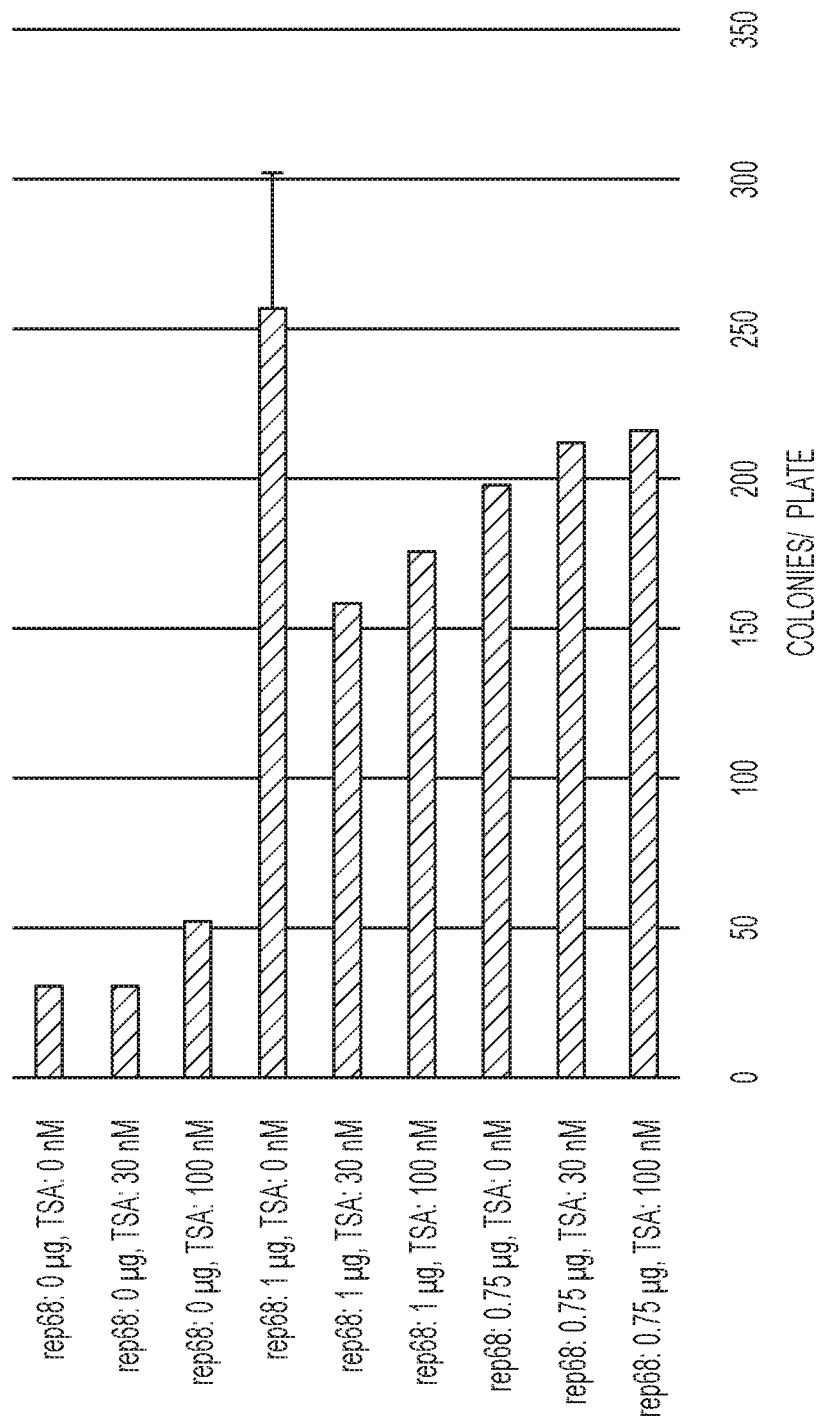
FIG. 1 is a quantification of HeLa S3 cell colonies that contain integrated rAAV genome after co-transfection of rAAV vectors with rep68 mRNA and/or TSA by electroporation. Results represent the number of colonies grown on day 10 after transfection on a 96 well plate. The number of colonies under the transfection condition of 1 µg of rep68 mRNA without TSA was an average from ten 96 well plates (+/− Standard Deviation)

The invention is based, in part, on the discovery that an HDAC inhibitor such as trichostatin A can be co-delivered with a recombinant polynucleotide to a eukaryotic cell, which can, for example, promote integration and/or expression of the polynucleotide in the eukaryotic cell. The invention is also based, in part, on the discovery that, a rep mRNA (e.g., rep68 and rep78) and/or an HDAC inhibitor can be co-delivered with a rAAV vector to a host cell and, for example, enhance delivery and integration of the rAAV into the host cell, amplification of the rAAV in the host cell and/or rAAV titer produced by the host cell.

Various features and aspects of the invention are discussed in more detail below.

I. Increasing Production of rAAV

One aspect of the invention provides a method of increasing rAAV titer or enhancing rAAV yield, e.g., from a eukaryotic or a host cell culture. The method includes co-delivering a rAAV vector with a rep mRNA (e.g., rep68 and/or rep78 mRNA) to a eukaryotic or host cell culture and harvesting rAAV from the cell culture. In certain embodiments, the method includes co-delivering a rAAV vector with a rep mRNA (e.g., rep68 and/or rep78 mRNA) to a eukaryotic or host cell culture, culturing the eukaryotic or host cell culture under conditions that allow for generation of rAAV, and harvesting the rAAV from the cell culture.

Another aspect of the invention provides a method of increasing rAAV vector titer or enhancing rAAV yield, e.g., from a eukaryotic or a host cell culture. The method includes co-delivering a rAAV vector with an HDAC inhibitor (e.g., TSA) to a eukaryotic or host cell culture and harvesting rAAV from the cell culture. In some embodiments, the method includes co-delivering a rAAV vector with an HDAC inhibitor (e.g., TSA) to a eukaryotic or host cell culture, culturing the eukaryotic or host cell culture under conditions that allow for generation of further rAAV, and harvesting the rAAV from the cell culture.

Another aspect of the invention provides a method of increasing rAAV vector titer or enhancing rAAV yield, e.g., from a eukaryotic or a host cell culture. The method includes co-delivering a rAAV vector with a rep mRNA (e.g., rep68 and/or rep78 mRNA) and an HDAC inhibitor (e.g., TSA) to a eukaryotic or host cell culture and harvesting rAAV from the cell culture. In some embodiments, the method includes co-delivering a rAAV vector with a rep mRNA (e.g., rep68 and/or rep78 mRNA) and an HDAC inhibitor (e.g., TSA) to a eukaryotic or host cell culture, culturing the eukaryotic or host cell culture under conditions that allow for generation of further rAAV, and harvesting the rAAV from the cell culture.

Adeno-associated virus (AAV) is a small, nonenveloped icosahedral virus of the genus Dependoparvovirus and family Parvovirus. It is capable of infecting both dividing and quiescent cells of several tissue types, with different AAV serotypes exhibiting different tissue tropism. AAV is non-autonomously replicating, and has a life cycle with a latent phase and an infectious phase. In the latent phase, after a cell is infected with an AAV, the AAV integrates into the host's genome as a provirus. In human cells, the preferential integration site resides on a region of roughly 2-kb on the long arm of chromosome 19 (19q13.3-qter). The infectious phase does not occur unless the cell is also infected with a helper virus (for example, adenovirus or herpes simplex virus), which activates AAV gene expression leading to the excision of the provirus DNA from the host cell chromosome, followed by replication and packaging of the viral genome. Upon helper virus-induced cell lysis, the newly assembled viruses are released.

Wild-type AAV has a single-stranded linear DNA genome of approximately 4.7 kb, which contains two 145 nucleotide-long inverted terminal repeats (ITRs) at the termini flanking the two viral genes—rep and cap. The rep gene, through the use of two promoters and alternative splicing, encodes four regulatory proteins—rep78, rep68, rep52 and rep40. These proteins are involved in AAV genome replication. The cap gene, through alternative splicing and initiation of translation, gives rise to three capsid proteins, VP1, VP2 and VP3. These proteins form the capsid of the AAV particle.

Given that the AAV ITRs contain all cis-acting elements involved in genome rescue, replication and packaging, and that the AAV ITRs are segregated from the viral encoding regions, i.e., rep and cap gene regions, some or all of the AAV 4.3 kb internal genome could be replaced with foreign DNA, for example, an expression cassette for an exogenous protein of interest to develop recombinant AAV (rAAV) vectors. rAAV vectors may have single-stranded genomes that are 4.7 kb in size, or are larger or smaller than 4.7 kb, including oversized genomes that are as large as 5.2 kb, or as small as 3.0 kb. Further, vector genomes may be substantially self-complementary, so that within the virus the genome is substantially double stranded. rAAV vectors containing genomes of all types are suitable for use in the method of the current invention.

AAV includes numerous serologically distinguishable types including serotypes AAV-1 to AAV-12, as well as more than 100 serotypes from nonhuman primates (See, e.g., Srivastava, J. Cell Biochem., 105(1): 17-24 (2008), and Gao et al., J. Virol., 78(12), 6381-6388 (2004)). AAV of any serotype may be used in the present invention, and a person of skill in the art will be able to identify AAV types suitable for the production of their desired rAAV vectors.

rAAV vectors can be co-delivered with a rep mRNA (e.g., rep68 mRNA and/or rep78 mRNA) to a cell culture, e.g., a host or eukaryotic cell culture, using any suitable method known in the art. rAAV vectors can be co-delivered an HDAC inhibitor to a cell culture, e.g., a host or eukaryotic cell culture, using any suitable method known in the art. rAAV vectors can be co-delivered with a rep mRNA (e.g., rep68 mRNA and/or rep78 mRNA) and an HDAC inhibitor to a cell culture, e.g., a host or eukaryotic cell culture, using any suitable method known in the art.

As used herein, a eukaryotic cell culture can be any cell or cells capable of producing a rAAV. In some embodiments, the host cell is a mammalian cell, for example, a HeLa cell, COS cell, HEK293 cell, A549 cell, BHK cell, or Vero cell. In other embodiments, the host cell is an insect cell, for example, a Sf9 cell, Sf-21 cell, Tn-368 cell, or BTI-Tn-5B1-4 (High-Five) cell (See e.g. U.S. Pat. Nos. 6,156,303, 5,387,484, 5,741,683, 5,691,176, 5,688,676, 8,163,543, U.S. Publication No. 20020081721, PCT Publication Nos. WO00/47757, WO00/24916, and WO96/17947). Unless otherwise indicated, the terms "cell" or "cell line" are understood to include modified or engineered variants of the indicated cell or cell line.

Rep mRNA (e.g., rep68 and/or rep78 mRNA can be produced, for example, by in vitro transcription (Howden et al, J Gene Med 2008; 10:42-50).

HDAC inhibitors as used herein can be inhibitors of any one of the four classes of HDACs. Exemplary HDAC inhibitors include trichostatin A (TSA), trapxin B, benzamides, phenylbutyraet, valproic acid, hydroxamic acid vorinostate (SAHA), belinostat, LAQ824, panobinostat, entinostat, CI994, mocetinostat, nicotinamide, dihydrocoumarin, naphthopyranone, and 2-hydroxynaphthaldehydes.

Methods of co-delivery vary depending on the target cells. Suitable methods include, for example: liposome-based transfection; chemical-based transfection, such as methods utilizing calcium phosphate, cationic polymers, DEAE-dextran, or activated dendrimers; microinjection; electroporation; magnetic beads; nanoparticles; or cell squeezing (see, for example, Ding et al. (2017) *Nat. Biomed. Eng.* 1:0039). A person of skill in the art will be able to identify suitable co-delivery methods and optimize the conditions according to the types of cells they intend to deliver rAAV vectors to.

In some embodiments, rAAV vectors are co-delivered to HelaS3 cells with rep68 mRNA using electroporation. In some embodiments, rAAV vectors are co-delivered to HelaS3 cells with an HDAC inhibitor, e.g., TSA, using electroporation. In some embodiments, rAAV vectors are co-delivered to HelaS3 cells with both rep68 mRNA and TSA using electroporation.

After delivery to eukaryotic cell cultures, rAAV vectors may be produced by the cells by many methods known in the art. To allow for production of rAAV, the host cell must be provided with AAV inverted terminal repeats (ITRs) (which may, for example, flank a heterologous nucleotide sequence of interest or an expression cassette encoding an exogenous protein of interest), AAV rep and cap gene functions, as well as additional helper functions. These can be provided to the host cell using a variety of appropriate plasmids or vectors. Additional helper functions can be provided by, for example, an adenovirus (AV) infection, by a plasmid that carries all of the required AV helper function genes, or by other viruses such as herpes simplex virus (HSV) or baculovirus. Any genes, gene functions, or other genetic material necessary for rAAV production by the host cell may transiently exist within the host cell, or be stably inserted into the host cell genome. In some embodiments, the host cell is a producer cell comprising AAV rep and cap gene functions and a rAAV vector genome. In some embodiments, the host cell is a packaging cell comprising AAV rep and cap gene functions, which at the time of production is provided a rAAV vector genome by a separate recombinant virus. rAAV production methods suitable for use with the methods of the current invention include those disclosed in Clark et al., Human Gene Therapy 6:1329-1341 (1995), Martin et al., Human Gene Therapy Methods 24:253-269 (2013), Thorne et al., Human Gene Therapy 20:707-714 (2009), Fraser Wright, Human Gene Therapy 20:698-706 (2009), and Virag et al., Human Gene Therapy 20:807-817 (2009).

rAAV particles may be obtained from host cells by lysing the cells. Lysis of AAV-infected cells can be accomplished by methods that chemically or enzymatically treat the cells in order to release infections viral particles. These methods include the use of nucleases such as benzonase or DNAse, proteases such as trypsin, or detergents or surfactants. Physical disruption, such as homogenization or grinding, or the application of pressure via a microfluidizer pressure cell, or freeze-thaw cycles may also be used. Alternatively, supernatant may be collected from AAV-infected cells without the need for cell lysis.

It may be necessary to purify the sample containing rAAV and helper virus particles to remove, for example, the cellular debris resulting from cell lysis. Methods of minimal purification of helper virus and AAV particles are known in the art, and any appropriate method can be used to prepare samples containing both AAV and helper virus particles for use in the methods of the present invention. Two exemplary purification methods are cesium chloride (CsCl)- and iodixanol-based density gradient purification. Both methods are described in Strobel et al., Human Gene Therapy Methods., 26(4): 147-157 (2015). Minimal purification can also be accomplished using affinity chromatography using, for example AVB Sepharose affinity resin (GE Healthcare Bio-Sciences AB, Uppsala, Sweden). Methods of AAV purification using AVB Sepharose affinity resin are described in, for example, Wang et al., Mol Ther Methods Clin Dev., 2:15040 (2015).

It may be necessary to inactivate helper virus by heat. Heat inactivation techniques are based on the different thermal stabilities of AAV and helper virus particles. For example, AAV particles can be heated to temperatures as high as 56° C. and still remain intact, while AV particles are rendered inactive. Conway et al., Gene Therapy 6,986-993, 1999, describes differential heat inactivation of HSV in AAV containing samples. Heat inactivation may be accomplished by any known methodology. In the examples described below, heat inactivation was accomplished using a thermocycler to rapidly heat and cool sample volumes of 300 μL or less. This system was chosen because it relies on heat transfer that is primarily conductive, making it a viable model for both continuous-flow systems and for larger batch systems that employ active mixing. Examples of continuous-flow systems include passage of the sample through a continuous-flow heat exchanger, such as the DHX™ Single-Use Heat Exchanger for Bio-therapeutic Manufacturing (Thermo Fisher Scientific, Millersburg, PA). Such systems allow the operator to control the heat inactivation process by controlling the flow rate of the sample through the heat exchanger, thus controlling the duration of the heating process, and the temperature of the heat exchanger, thus controlling the temperature of heat inactivation.

Alternatively, heat inactivation may be accomplished using batch systems of various sizes. For example, heat inactivation may be accomplished at the 1 L scale, by placing the AAV containing sample in a 1 L PETG bottle and placing the bottle in a water bath set at the desired inactivating temperature for the desired period of time, with mixing, for example, the samples may be heated to 47° C. for 20 minutes. At a larger scale, heat inactivation may be accomplished by placing the rAAV containing sample in a 5 L bioprocessing bag on a temperature controlled rocking platform set at the desired inactivating temperature, for the desired period of time. For example, the rocking platform may be set to 49° C. at a rocking speed of 30 RPM, with a 12° angle of mixing for 40 minutes.

Heat inactivation may occur at any temperature where there is a sufficient difference in stability between rAAV particles and helper virus particles that helper virus particles are substantially inactivated while active rAAV particles remain. A person of skill in the art will understand that higher temperatures may be required to achieve greater levels of AV reduction.

Once heat inactivation has been accomplished, it may be necessary or desirable to determine the efficiency of inactivation. The efficacy of an inactivation protocol is determined by assays that detect the presence of replication competent helper virus, such as a plaque assay. Plaque assays for helper virus are well known to those in the art, including plaque assays for AV, HSV, baculovirus, and others. Plaque assays of adenovirus may be conducted using any appropriate cell type, for example HeLa or HEK293 cells. Standard plaque assay protocols are described in, for example, Current Protocols in Human Genetics, 2003. Alternative assays for measuring adenoviral titers include those that allow the identification of infected cells in culture by detecting viral proteins, such as hexon proteins, using immunocytochemical staining. Such assays include the QuickTiter™ Adenovirus Titer Immunoassay Kit (Cell Biolabs, San Diego, CA). The efficiency of inactivation is generally reported as the log reduction of virus (LRV).

Quantification of rAAV particles is complicated by the fact that AAV infection does not result in cytopathic effect in vitro, and therefore plaque assays cannot be used to determine infectious titers. AAV particles can be quantified using a number of methods, however, including quantitative polymerase chain reaction (qPCR) (Clark et al., Hum. Gene Ther. 10, 1031-1039 (1999)) or dot-blot hybridization (Samulski et al., J. Virol. 63, 3822-3828 (1989)), or by optical density of highly purified vector preparations (Sommer et al., Mol. Ther. 7, 122-128 (2003)). DNase-resistant particles (DRP) can be quantified by real-time quantitative polymerase chain reaction (qPCR) (DRP-qPCR) in a thermocycler (for example, an iCycler iQ 96-well block format thermocycler (Bio-Rad, Hercules, CA)). Samples containing AAV particles are incubated in the presence of DNase I (100 U/ml; Promega, Madison, WI) at 37° C. for 60 min, followed by proteinase K (Invitrogen, Carlsbad, CA) digestion (10 U/ml) at 50° C. for 60 min, and then denatured at 95° C. for 30 min. The primer-probe set used should be specific to a non-native portion of the AAV vector genome, for example, the poly(A) sequence of the protein of interest. The PCR product can be amplified using any appropriate set of cycling parameters, based on the length and composition of the primers, probe, and amplified sequence. Alternative protocols are disclosed in, for example, Lock et al., Human Gene Therapy Methods 25(2): 115-125 (2014).

The infectivity of rAAV particles can be determined using a $TCID_{50}$ (tissue culture infectious dose at 50%) assay, as described for example in Zhen et al., Human Gene Therapy 15:709-715 (2004). In this assay, AAV vector particles are serially diluted and used to co-infect a rep/cap-expressing cell line along with AV particles in 96-well plates. 48 hours post-infection, total cellular DNA from infected and control wells is extracted. AAV vector replication is then measured using qPCR with transgene-specific probe and primers. $TCID_{50}$ infectivity per milliliter ($TCID_{50}$/ml) is calculated with the Kärber equation, using the ratios of wells positive for AAV at 10-fold serial dilutions.

II. Generating Stable Cell Lines

Another aspect of the invention provides a method of generating or developing a cell line, e.g., a stable cell line for producing recombinant AAV (rAAV). The method includes co-delivering a rAAV vector with a rep mRNA (e.g., rep68 and/or rep78 mRNA) to a eukaryotic or host cell culture, followed by identifying a eukaryotic or host cell that contains the rAAV vector sequence integrated into the eukaryotic or host cell genome (e.g., by selecting cell colonies that have the rAAV vector integrated into the eukaryotic or host cell genome) and, optionally, harvesting the rAAV from the cell culture. In some embodiments, the method includes co-delivering a rAAV vector with a rep mRNA to a eukaryotic or host cell culture, culturing the eukaryotic or host cell culture under conditions that allow for integration of the rAAV vector into the eukaryotic or host cell genome, identifying a eukaryotic or host cell that contains the rAAV vector sequence integrated into the eukaryotic or host cell genome, culturing the eukaryotic or host cell under conditions that allow for generation of further rAAV, and, optionally, harvesting the rAAV from the cell culture. In some embodiments, co-delivery of the rAAV with the rep mRNA enhances integration of rAAV vector into the eukaryotic or host cell genome. In some embodiments, co-delivery of the rAAV with the rep mRNA enhances the titer of the harvested rAAV.

Another aspect of the invention provides a method of generating or developing a cell line, e.g., a stable cell line for producing recombinant AAV (rAAV). The method includes co-delivering a rAAV vector with an HDAC inhibitor (e.g., TSA) to a eukaryotic or host cell culture, followed by identifying a eukaryotic or host cell that contains the rAAV vector sequence integrated into the eukaryotic or host cell genome (e.g., by selecting cell colonies that have the rAAV vector integrated into the eukaryotic or host cell genome) and, optionally, harvesting the rAAV from the cell culture. In some embodiments, the method includes co-delivering a rAAV vector with an HDAC inhibitor (e.g., TSA) to a eukaryotic or host cell culture, culturing the eukaryotic or host cell culture under conditions that allow for integration of the rAAV vector into the eukaryotic or host cell genome, identifying a eukaryotic or host cell that contains the rAAV vector sequence integrated into the eukaryotic or host cell genome, culturing the eukaryotic or host cell under conditions that allow for generation of further rAAV, and, optionally, harvesting the rAAV from the cell culture. In some embodiments, co-delivery of the rAAV with the HDAC inhibitor (e.g., TSA) enhances integration of rAAV vector into the eukaryotic or host cell genome. In some embodiments, co-delivery of the rAAV with the HDAC inhibitor (e.g., TSA) enhances the titer of the harvested rAAV.

Another aspect of the invention provides a method of generating or developing a cell line, e.g., a stable cell line for producing recombinant AAV (rAAV). The method includes co-delivering a rAAV vector with a rep mRNA (e.g., rep68 and/or rep78 mRNA) and an HDAC inhibitor (e.g., TSA) to a eukaryotic or host cell culture, followed by identifying a eukaryotic or host cell that contains the rAAV vector sequence integrated into the eukaryotic or host cell genome (e.g., by selecting cell colonies that have the rAAV vector integrated into the eukaryotic or host cell genome) and, optionally, harvesting the rAAV from the cell culture. In some embodiments, the method includes co-delivering a rAAV vector with a rep mRNA (e.g., rep68 and/or rep78 mRNA) and an HDAC inhibitor (e.g., TSA) to a eukaryotic or host cell culture, culturing the eukaryotic or host cell culture under conditions that allow for integration of the rAAV vector into the eukaryotic or host cell genome, identifying a eukaryotic or host cell that contains the rAAV vector sequence integrated into the eukaryotic or host cell genome, culturing the eukaryotic or host cell under conditions that allow for generation of further rAAV, and, optionally, harvesting the rAAV from the cell culture. In some embodiments, co-delivery of the rAAV with the rep mRNA (e.g., rep68 and/or rep78 mRNA) and the HDAC inhibitor (e.g., TSA) enhances integration of rAAV vector into the eukaryotic or host cell genome. In some embodiments, co-delivery of the rAAV with the rep mRNA (e.g., rep68 and/or rep78 mRNA) and the HDAC inhibitor (e.g., TSA) enhances the titer of the harvested rAAV.

Another aspect of the invention provides a method of generating or developing a cell line, e.g., a stable cell line for producing recombinant AAV (rAAV). The method includes co-delivering a rAAV vector with a rep mRNA (e.g., rep68 and/or rep78 mRNA) and an HDAC inhibitor (e.g., TSA) to a eukaryotic or host cell culture, followed by identifying a eukaryotic or host cell that contains the rAAV vector sequence integrated into the eukaryotic or host cell genome (e.g., by selecting cell colonies that have the rAAV vector integrated into the eukaryotic or host cell genome) and, optionally, harvesting the rAAV from the cell culture.

After transfection, integration of the rAAV into the host genome can be assayed by various methods, such as antibiotic selection, fluorescence-activated cell sorting, southern blot, PCR based detection, fluorescence in situ hybridization as described by Nakai et al, Nature Genetics (2003) 34, 297-302; Philpott et al, Journal of Virology (2002) 76(11): 5411-5421, and Howden et al, J Gene Med 2008; 10:42-50. Furthermore, stable cell lines can be established according to protocols well known in the art, such as those described in Clark, Kidney International Vol 61 (2002):S9-S15, and Yuan et al, Human Gene Therapy 2011 May; 22(5):613-24.

III. Co-Delivering Recombinant Polynucleotides with HDAC Inhibitors

Another aspect of the invention provides a method including co-delivering a recombinant polynucleotide with an HDAC inhibitor such as trichostatin A (TSA) to a eukaryotic or a host cell culture. In some embodiments, the method includes co-delivering a recombinant polynucleotide with an HDAC inhibitor to a eukaryotic or a host cell culture, culturing the eukaryotic or host cell culture under conditions that allow for integration of the polynucleotide into the eukaryotic or host cell genome, detecting the integration of the polynucleotide into the eukaryotic or host cell genome, and/or generating a stable eukaryotic or host cell line.

In some embodiments, one or more gene products are expressed in the eukaryotic or host cell culture. The gene products can be encoded by the recombinant polynucleotide or indirectly dependent on the presence of the recombinant polynucleotide. The gene products can be, for example, ribonucleic acids, peptides, or proteins.

In some embodiments, the recombinant polynucleotide is a viral vector, for example, a rAAV vector. Co-delivery of a recombinant viral vector with an HDAC inhibitor may enhance the integration of the viral vector into the host cell genome and increase the yield of virus harvested from the host cell.

Recombinant polynucleotides as used herein can be DNA, RNA, hybrids, and chimeras thereof. They may be single-stranded or double-stranded. In some embodiments, they may be an expression vector in which a nucleotide sequence encoding a desired protein is integrated downstream of the nucleotide sequence encoding the signal peptide, and is capable of high-level expression of the protein downstream of the nucleotide sequence of the signal peptide. The present invention is suitable for any vectors such as commonly used plasmids and viruses. Examples of such vectors may include pUC19, pUC18, pBR322, pHSG299, pHSG298, pHSG399, pHSG398, RSF1010, pMW119, pMW118, pMW219, pMW218, and vectors based on adeno-associated virus, adenovirus, lentivirus, and retrovirus. The recombinant polynucleotide of the present invention may further incorporate other nucleotide sequences commonly used in expression vectors, such as a promoter, terminator, Kozak sequence, multicloning site, drug-resistant gene, and other nucleotide sequences.

HDAC inhibitors as used herein can be inhibitors acting on any one of the four classes of HDACs. Examples include trichostatin A, trapxin B, benzamides, phenylbutyraet, valproic acid, hydroxamic acids vorinostat (SAHA), belinostat (PXD101), LAQ824, panobinostat (LBH589), entinostat (MS-275), CI994, mocetinostat (MGCD0103), nicotinamide, dihydrocoumarin, naphthopyranone, and 2-hydroxynaphthaldehydes.

The HDAC inhibitor and the recombinant polynucleotide could be coadministered to any eukaryotic cell culture, including cell lines of mammalian origin, insect origin or yeast origin; primary cells or stem cells capable of growth in culture, Co-delivery methods of polynucleotides and an HDAC inhibitor depend largely on the target cell types and polynucleotides. They can include: liposome-based transfection; chemical-based transfection, such as methods utilizing calcium phosphate, cationic polymers, DEAE-dextran, or activated dendrimers; microinjection; electroporation; magnetic beads; nanoparticles; or cell squeezing. A person of skill in the art will be able to identify suitable co-delivery methods according to the types of cells to which they intend to deliver the polynucleotides.

After co-delivering polynucleotides with an HDAC inhibitor into a eukaryotic cell culture, integration of the polynucleotides into the host genome can be assayed by various methods well known in the art, such as antibiotic selection, fluorescence-activated cell sorting, PCR based method, fluorescence in situ hybridization as descried by Wang et al, *Gene Therapy* (2004) 11, 711-721; Philpott et al, Journal of Virology (2002) 76(11):5411-5421; Howden et al, J Gene Med 2008; 10:42-50. In addition, stable cell lines can be established according to protocols described in Longo et al. Methods Enzymol 2013; 529: 209-226; and Yuan et al, Human Gene Therapy 2011 May; 22(5):613-24. In some embodiments, one or more gene products in the host cells are expressed. The gene products can be encoded by the recombinant polynucleotides or indirectly dependent on the presence of the recombinant polynucleotides introduced into the host cells. The gene products which vary from ribonucleic acids, peptides, to proteins can be detected by methods well established in the art, such as RT-PCR, Northern blot, Western blot, Southern blot, immunofluorescence and ELISA. In some embodiments, the polynucleotides are viral vectors, and their production, isolation, and quantification are known in the art.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/ or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

Practice of the invention will be more fully understood from the foregoing examples, which are presented herein for illustrative purposes only, and should not be construed as limiting the invention in any way.

EXAMPLES

Colony Formation

HeLa S3 cells cultured in suspension were plated one day before transfection to allow them to adapt to adherent culture condition. On the day of transfection, 15 μg of rAAV vectors were mixed with 0, 0.75 or 1 μg of rep68 mRNA in combination with 0, 30 nM or 100 nM trichostatin A (TSA) and then transfected into $10^6$ cells by electroporation at 100 V for 30 ms in 0.2 cm gap cuvettes. After electroporation, cells were incubated at room temperature for 5 min before being plated on a 96 well plate with DMEM media containing 10% FBS. 24 hours after transfection, media containing 400 ng/ml puromycin were used to select cells that have rAAV vectors integrated into their genome. The number of colonies grown on day 10 after transfection was counted on each plate. FIG. 1 shows quantification of cell colonies after co-delivery of rAAV vectors with various amounts of rep68 mRNA and/or TSA. Results represent the number of colonies grown after plating on a 96 well plate and antibiotic selection. The number of colonies under the transfection condition of 1 μg of rep68 without TSA was an average from ten 96 well plates (+/− Standard Deviation). Results show that co-transfection of rAAV vectors with rep68 mRNA significantly enhanced colony formation, and TSA also moderately increased colony formation.

rAAV Production

Figure 2:
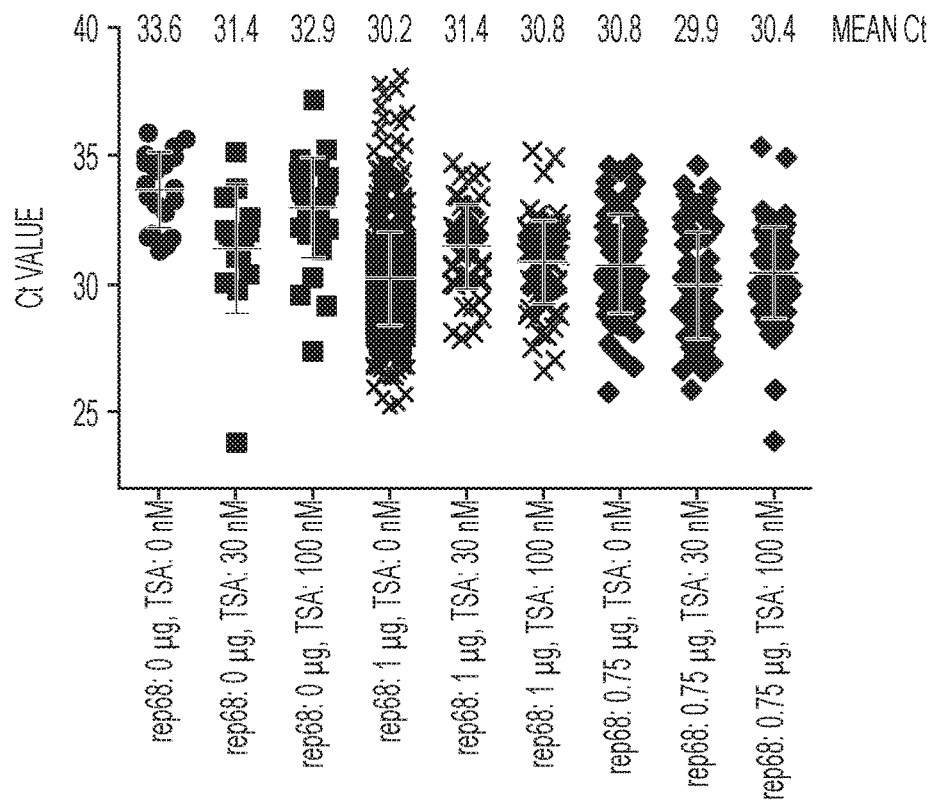
FIG. 2 shows quantification of DNase-Resistant Particles by qPCR. rAAV was produced by Hela S3 colonies established after co-delivery of rAAV vectors with rep68 mRNA and/or TSA by electroporation. Lower $C_t$ value indicates higher yield of rAAV produced from the host cells. Mean $C_t$ values and distributions of $C_t$ values are shown.

On day 15 after the co-transfection described above, colonies formed on the 96 well plate were infected with adenovirus 5 (Ad5) at a Multiplicity of Infection (MOI) of 30 to enable formation of viral particles. On day 18, the infected cells were lysed for 2 hours at 3° C. in lysis buffer containing sodium deoxycholate and Benzonase. Supernatants from the samples were sequentially digested with DNase I and then Proteinase K to liberate rAAV genomic DNA. TaqMan qPCR amplifying the BGH-PolyA coding region of the rAAV vector was then used to determine the $C_t$ value of each sample. FIG. 2 shows distributions of the $C_t$ values of colonies and the mean $C_t$ value under each co-transfection condition. Co-delivery of rAAV with 1 μg rep68 mRNA+30 nM TSA, or 0.75 μg rep68 mRNA+100 nM TSA led to decreased $C_t$ values, indicating enhanced rAAV production from the host cells under these transfection conditions.

Generation of Stable Cell Lines

Figure 3:
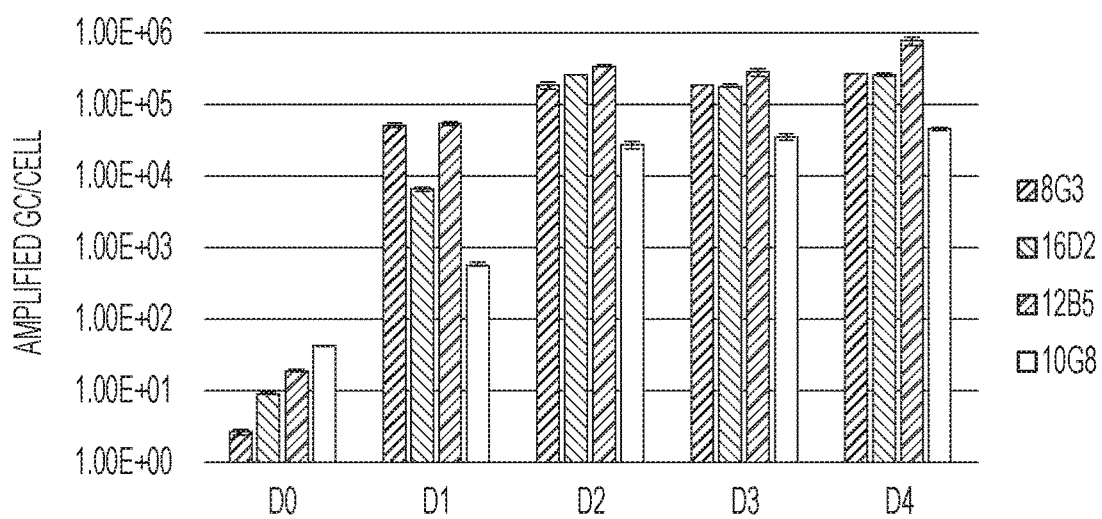
FIG. 3 shows amplified rAAV genome copy (GC) assayed by qPCR in four cell lines derived from HeLa cells after co-transfection of rAAV vectors with rep68 mRNA and/or TSA: 1 μg rep68 mRNA–8G3 clone, 30 nM TSA–12B5 clone, and 0.75 μg rep68 mRNA+100 nM TSA–16D2 clone. Cell line 10G8 was established after transfection of rAAV vectors alone. After infection with an adenoviral helper virus, cells were collected on days 0, 1, 2, 3, and 4 (D0, D1, D2, D3, D4) post-infection, from which genomic DNA was isolated for the assay. Error bars indicate standard deviations from triplicates of qPCR.
Figure 4:
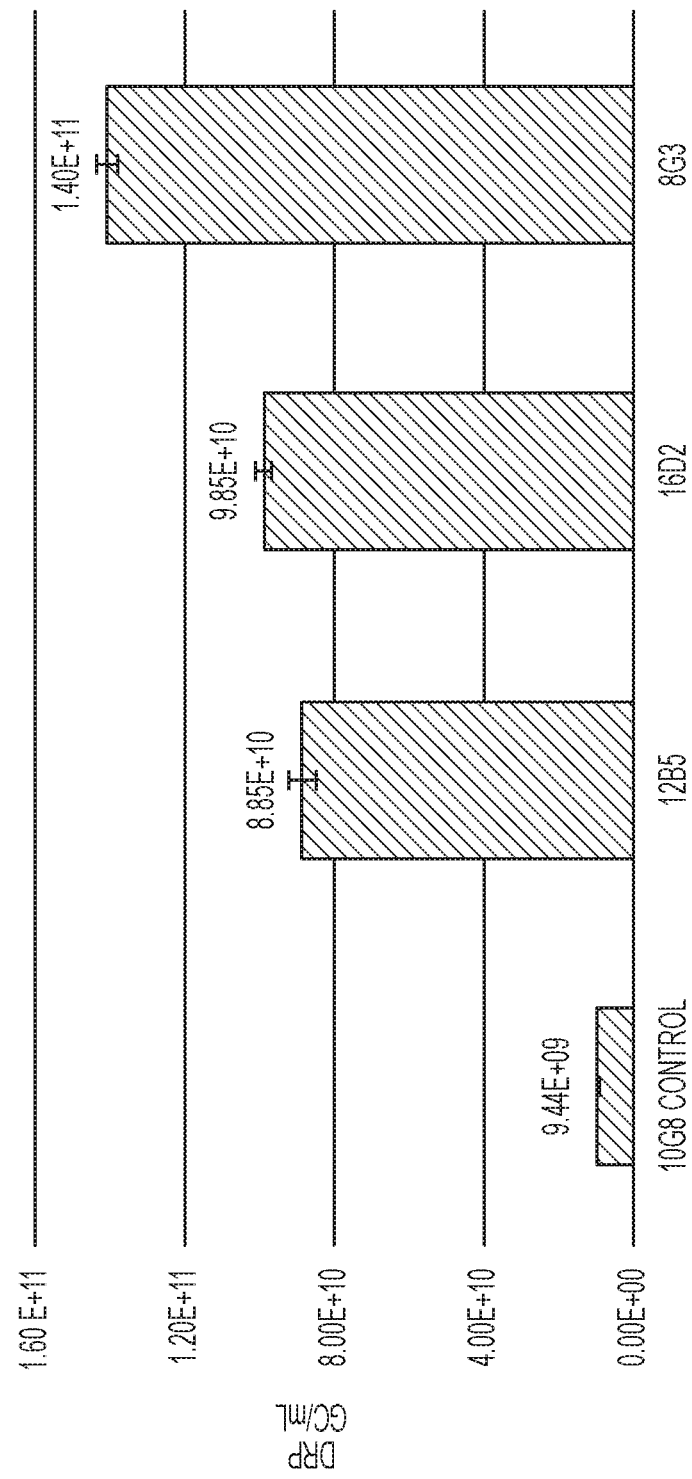
FIG. 4 shows rAAV titers produced in the same four cell lines described in FIG. 3. After the helper virus infection, supernatants were collected from the cells, and DNase-Resistant Particles (DRP) were quantified by qPCR giving rAAV genome copy per ml (GC/ml) of supernatant.

Stable cell lines were generated from different rAAV co-transfection conditions as described above: 1 μg rep68 mRNA (8G3 clone), 30 nM TSA (12B5 clone), or 0.75 μg rep68 mRNA+100 nM TSA (16D2 clone) together with a control cell line generated by transfection of rAAV vector without rep mRNA or TSA (10G8 clone). After infection with Ad5 at an MOI of 50, cells were collected on days 0, 1, 2, 3, and 4 (D0, D1, D2, D3, D4) post-infection, from which genomic DNA was isolated. TaqMan qPCR was used to amplify the rAAV genome as well as an endogenous gene—RNase P. Quantification of rAAV genome copy number per cell (GC/cell) was accomplished by normalization with RNase P gene, which is present at approximately three copies in each HeLa cell. FIG. 3 shows increased rAAV genome copy in the stable cell lines derived by co-transfection of rAAV vectors and rep68 mRNA and/or TSA compared with the cell line transfected with rAAV alone, indicating that rep68 mRNA and/or TSA improved integration of rAAV genome into host cells and stable host cell line generation.

rAAV Yield from Stable Cell Lines rAAV yield was assayed from the control and three stable cell lines described above. Cells were seeded in duplicate flasks at $1.5 \times 10^6$ cells/mL in 100 mL of Production Medium (90 mL Suspension DMEM+10 mL EX-CELL) and infected with Ad5 at an MOI of 50. Four days after infection, cells were lysed for 2 hours at 3° C. in lysis buffer containing sodium deoxycholate and Benzonase®. Supernatant from the samples were sequentially digested with DNase I and then Proteinase K to liberate rAAV genomic DNA. TaqMan qPCR amplifying the BGH-PolyA coding region of the rAAV genome was then used to determine the rAAV genome copy number (GC) based on a rAAV plasmid standard curve. FIG. 4 shows enhanced production of rAAV from stable cell lines established by co-delivery of rAAV vectors and rep68 mRNA and/or TSA, suggesting that co-delivery of rAAV vectors with rep68 mRNA and/or TSA to host cells improved rAAV production from the host cells.

NUMBERED EMBODIMENTS

1. A method of increasing recombinant AAV (rAAV) vector titer, the method comprising:
   a) co-delivering a rAAV vector with a rep mRNA to a eukaryotic cell culture; and
   b) harvesting rAAV from the eukaryotic cell culture, wherein the co-delivery with the rep mRNA increases the titer of the harvested rAAV.
2. The method of embodiment 1, wherein the rep mRNA is selected from the group consisting of rep68 mRNA and rep78 mRNA.
3. The method of embodiment 1, wherein the co-delivering comprises electroporation.
4. The method of embodiment 1, wherein the co-delivering involves magnetic beads.
5. The method of embodiment 1, wherein the co-delivering involves nanoparticles.
6. The method of embodiment 1, wherein the co-delivering comprises microinjection.
7. The method of embodiment 1, wherein the co-delivering comprises cell squeezing.
8. The method of embodiment 1, wherein the co-delivering comprises chemical-based transfection.
9. The method of embodiment 8, wherein the chemical-based transfection comprises exposure to lipids.
10. The method of embodiment 8, wherein the chemical-based transfection comprises exposure to calcium phosphate.
11. The method of embodiment 8, wherein the chemical-based transfection comprises exposure to cationic polymers.
12. The method of embodiment 8, wherein the chemical-based transfection comprises exposure to DEAE-dextran.
13. The method of embodiment 8, wherein the chemical-based transfection comprises exposure to activated dendrimers.
14. A method of developing a cell line for producing recombinant AAV (rAAV), the method comprising:
   a) co-delivering a rAAV vector with a rep mRNA to eukaryotic cells;
   b) identifying a eukaryotic cell that contains the rAAV vector sequence integrated into the eukaryotic cell genome; and
   c) optionally harvesting rAAV from a culture comprising the eukaryotic cell, wherein the co-delivery with the rep mRNA enhances the titer of the harvested rAAV.
15. The method of embodiment 14, wherein the rep mRNA is selected from the group consisting of rep68 mRNA and rep78 mRNA.
16. The method of embodiment 14, wherein the co-delivering comprises electroporation.
17. The method of embodiment 14, wherein the co-delivering involves magnetic beads.
18. The method of embodiment 14, wherein the co-delivering involves nanoparticles.
19. The method of embodiment 14, wherein the co-delivering comprises microinjection.
20. The method of embodiment 14, wherein the co-delivering comprises cell squeezing.
21. The method of embodiment 14, wherein the co-delivering comprises chemical-based transfection.
22. The method of embodiment 21, wherein the chemical-based transfection comprises exposure to lipids.
23. The method of embodiment 21, wherein the chemical-based transfection comprises exposure to calcium phosphate.
24. The method of embodiment 21, wherein the chemical-based transfection comprises exposure to cationic polymers.
25. The method of embodiment 21, wherein the chemical-based transfection comprises exposure to DEAE-dextran.
26. The method of embodiment 21, wherein the chemical-based transfection comprises exposure to activated dendrimers.
27. A method comprising co-delivering an HDAC inhibitor and a recombinant polynucleotide to eukaryotic cells.
28. The method of embodiment 27, further comprising the step of detecting integration of the recombinant polynucleotide within a chromosome of one of the eukaryotic cells.
29. The method of embodiment 27 or 28, further comprising the step of establishing a stable cell line with the recombinant polynucleotide integrated into the eukaryotic cell genome.
30. The method of any one of embodiments 27-29, further comprising a step of expressing a gene product dependent on the presence of the recombinant polynucleotide within the eukaryotic cell.
31. The method of embodiment 30, wherein the gene product is a ribonucleic acid.
32. The method of embodiment 30, wherein the gene product is a polypeptide.
33. The method of embodiment 30, wherein the polynucleotide encodes the gene product.
34. The method of embodiment 30, wherein the polynucleotide comprises a recombinant viral vector.
35. The method of embodiment 34, wherein the recombinant viral vector is an adeno-associated viral vector (AAV vector).
36. The method of embodiment 34, further comprising the step of harvesting the recombinant virus from a culture of the eukaryotic cells.
37. The method of embodiment 35, further comprising the step of harvesting the recombinant AAV from a culture of the eukaryotic cells.
38. The method of embodiment 27, wherein the co-delivering comprises electroporation.
39. The method of embodiment 27, wherein the co-delivering involves magnetic beads.
40. The method of embodiment 27, wherein the co-delivering involves nanoparticles.
41. The method of embodiment 27, wherein the co-delivering comprises microinjection.
42. The method of embodiment 27, wherein the co-delivering comprises cell squeezing.
43. The method of embodiment 27, wherein the co-delivering comprises chemical-based transfection.

44. The method of embodiment 43, wherein the chemical-based transfection comprises exposure to lipids.
45. The method of embodiment 43, wherein the chemical-based transfection comprises exposure to calcium phosphate.
46. The method of embodiment 43, wherein the chemical-based transfection comprises exposure to cationic polymers.
47. The method of embodiment 43, wherein the chemical-based transfection comprises exposure to DEAE-dextran.
48. The method of embodiment 43, wherein the chemical-based transfection comprises exposure to activated dendrimers.
49. The method according to any one of embodiments 27-48, wherein the HDAC inhibitor is trichostatin A.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of developing a stable cell line comprising a recombinant AAV (rAAV) vector sequence stably integrated into chromosome 19 for producing rAAV, the method comprising:
   a) providing a rAAV vector comprising the rAAV vector sequence and a rep mRNA selected from the group consisting of rep68 mRNA, rep78 mRNA, and a combination thereof to a HeLa cell culture;
   b) culturing the HeLa cell culture under conditions that allow for integration of the rAAV vector into the HeLa cell genome;
   c) identifying a HeLa cell that contains the rAAV vector sequence integrated into chromosome 19 of the HeLa cell genome; and
   d) culturing the mammalian cell under conditions that allow for generation of a cell line that produces rAAV, wherein the rAAV produced by the cell line is at a titer of at least $8.5 \times 10^{10}$ GC/ml when the HeLa cell culture of d) is cultured for at least four days.

2. The method of claim 1, wherein the delivering of the rAAV vector and the rep mRNA is performed using electroporation, chemical-based transfection, microinjection, or cell squeezing.

3. The method of claim 2, wherein the chemical-based transfection comprises exposure to lipids, calcium phosphate, cationic polymers, DEAE-dextran, or activated dendrimers.

4. The method of claim 1, wherein the delivering of the rAAV vector and the rep mRNA is performed using magnetic beads or nanoparticles.

5. The method of claim 1, wherein the rAAV vector sequence is integrated into the HeLa cell genome at a 2-kb region on the long arm of chromosome 19 (19q13.3-qter).

6. The method of claim 1, wherein the amount of rep mRNA provided to the HeLa cell is between 0.75 µg to 1 µg per $10^6$ cells.

7. The method of claim 1, wherein the rAAV produced by the HeLa cell line is at a titer of about $8.85 \times 10^{10}$ GC/ml to about 1.4 to $10^{11}$ GC/ml.

8. A stable HeLa cell line generated using the method of claim 1.

9. A plurality of rAAV particles produced by the stable HeLa cell line developed using the method of claim 1.

10. The method of claim 1, wherein the HeLa cell culture is a HeLa S3 cell culture.

* * * * *